(12) United States Patent
Thompson et al.

(10) Patent No.: US 11,571,654 B2
(45) Date of Patent: Feb. 7, 2023

(54) ETHYLENE SEPARATIONS USING A SMALL PORE ZEOLITE WITH CDO FRAMEWORK

(71) Applicant: CHEVRON U.S.A. INC., San Ramon, CA (US)

(72) Inventors: Joshua A. Thompson, Martinez, CA (US); Joel E. Schmidt, Oakland, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 0 days.

(21) Appl. No.: 17/392,354

(22) Filed: Aug. 3, 2021

(65) Prior Publication Data

US 2022/0072468 A1 Mar. 10, 2022

Related U.S. Application Data

(60) Provisional application No. 63/075,376, filed on Sep. 8, 2020.

(51) Int. Cl.
*B01D 53/047* (2006.01)
*C07C 7/13* (2006.01)

(52) U.S. Cl.
CPC .............. *B01D 53/047* (2013.01); *C07C 7/13* (2013.01); *B01D 2253/108* (2013.01); *B01D 2256/24* (2013.01); *B01D 2257/102* (2013.01); *B01D 2257/108* (2013.01); *B01D 2257/7022* (2013.01); *B01D 2259/402* (2013.01); *B01D 2259/40013* (2013.01); *B01D 2259/40035* (2013.01)

(58) Field of Classification Search
CPC .................. B01D 53/02; B01D 53/047; B01D 2253/108; B01D 2253/1085; B01D 2256/24; B01D 2257/102; B01D 2257/108; B01D 2257/7022; B01D 2259/40013; B01D 2259/40035; B01D 2259/40052; B01D 2259/402; C07C 7/12; C07C 7/13; C07C 11/04
See application file for complete search history.

(56) References Cited

PUBLICATIONS

Ikeda et al. ("The Topotactic Conversion of a Novel Layered Silicate into a New Framework Zeolite." Angew. Chem. Int. Ed. 2004, 43, 4892-4896 (Year: 2004).*

* cited by examiner

*Primary Examiner* — Youngsul Jeong
*Assistant Examiner* — Jason Y Chong
(74) *Attorney, Agent, or Firm* — Howard Owens

(57) ABSTRACT

The present invention, and embodiments thereof, provide a process to separate ethylene products from impurities such as nitrogen, hydrogen, ethane, propane and isobutane without the need for distillation processes.

4 Claims, 9 Drawing Sheets

ETHYLENE SEPARATIONS USING A SMALL PORE ZEOLITE WITH CDO FRAMEWORK

BACKGROUND

Ethylene-ethane separations for current commercial applications require the use of very large distillation towers and energy requirements in order to separate ethylene to a polymer-grade level. In the polyethylene plant there are stranded gas streams containing significant ethylene content, ranging from 50 to greater than 90 mol %. Due to the intensive process currently used, these gas streams cannot be recycled or recovered at smaller scales. In prior art, some membrane technologies have been developed that have moderate ethylene membrane selectivity, typically less than 10.

Pressure-swing adsorption (PSA) technology is an alternative technology for recovering stranded ethylene in a polyethylene plant that uses a solid adsorbent material to remove impurities that include ethane, hydrogen, nitrogen and methane gas. The adsorbent selection can function as either an equilibrium-based or kinetic-based separation. In principle, all adsorption processes utilize at least two steps: adsorption or uptake of the target molecule in the adsorbent; and desorption or removal of the same target molecule from the adsorbent. This may be achieved by changes in concentration, pressure, or temperature. In the case of PSA and vacuum-swing adsorption (VSA), pressure changes are used to regenerate the adsorbent. PSA does not require a dehydration step necessarily prior to separation of target components. PSA technology is able to treat stranded ethylene gas to recover ethylene up to a target purity of at least 98 mol % without the use of distillation or other thermally-driven separation processes.

It would be desirable to have a PSA or VSA process utilizing an adsorbent material which would require lower vacuum power consumption or elimination of vacuum entirely while allowing for improved recovery of ethylene product. Such a process would enable deployment and competitive use of PSA units to recover stranded ethylene gases.

In one aspect, a method is provided for removing impurities found in a polyethylene plant from a stranded ethylene gas stream. These impurities include methane, nitrogen, hydrogen and ethane, but may also include propane and isobutane. The method includes alternating input of the feed gas stream between at least two beds of adsorbent particles comprising a zeolite with CDO framework such that the feed gas stream contacts one of the at least two beds at a given time in an adsorption step and a tail gas stream is simultaneously vented from another of the at least two beds in a desorption step. The contact occurs at a feed pressure of from about 50 to about 500 psia for a sufficient period of time to preferentially adsorb ethylene over other impurities in the gas stream. A product gas stream is produced containing no greater than 2 mol % of impurities and at least 98 mol % purity of ethylene. The feed gas stream is input at a feed end of each bed. The product gas stream is removed by depressurization of the bed and desorption of ethylene adsorbed on the zeolite adsorbent with CDO framework. The impurity stream is produced in less than the feed composition of ethylene and utilized as a fuel gas or other gas stream within the polyethylene plant.

SUMMARY

An embodiment of the invention is methods using alternative adsorbent particles that comprise a zeolite with CDO framework to remove the contaminants from a feed gas stream.

A further embodiment of the invention is a method of using zeolite particles comprised of a CDO framework as an adsorbent material in a cyclic adsorption process for upgrading ethylene product from at least 50 mol % to at least 98 mol %.

DETAILED DESCRIPTION

Figure 1:
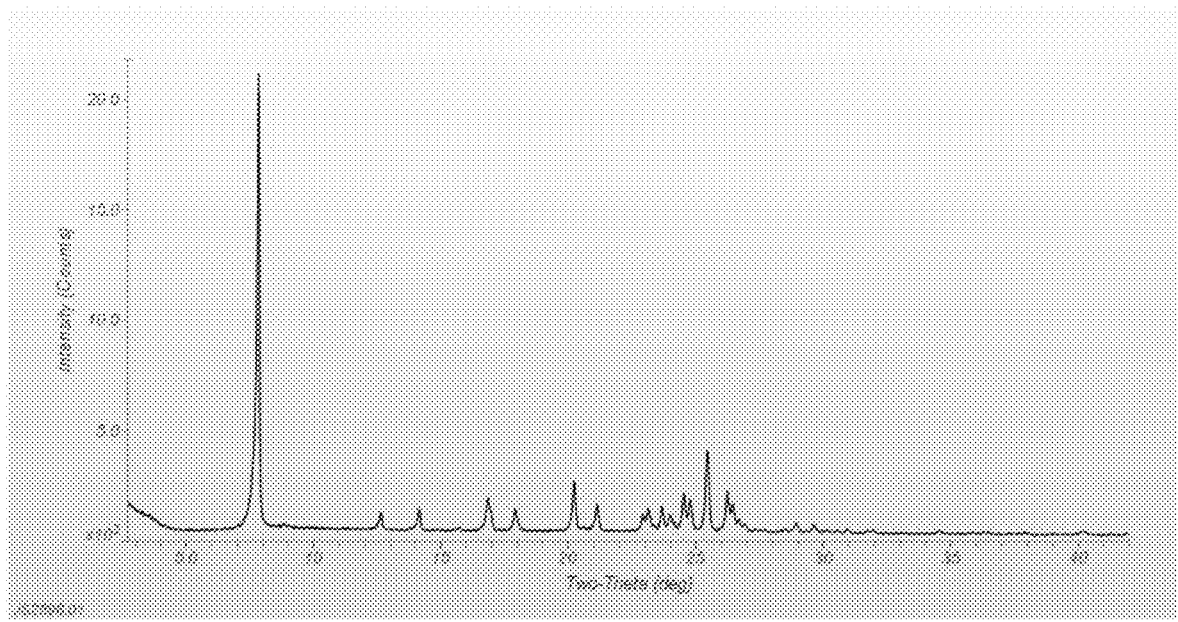
FIG. 1 is a XRD pattern of as made RUB-36.

The methods of the present disclosure use zeolite particles comprised of a CDO framework as an adsorbent material in a cyclic adsorption process for upgrading ethylene product from at least 50 mol % to at least 98 mol %. The other components in the stream can be ethane and larger hydrocarbons as well as N2, CH4 and H2.

In one embodiment, methods and processes of the present disclosure use alternative adsorbent particles that comprise a zeolite with CDO framework to remove the contaminants from a feed gas stream. Zeolites are crystalline solid structures made of silicon, aluminum and oxygen that form a framework with cavities and channels inside where cations, water and/or small molecules may reside. Zeolites are crystalline aluminosilicates with open 3D framework structures built of SiO4 and AlO4 tetrahedra linked to each other by sharing all the oxygen atoms to form regular intra-crystalline cavities and channels of molecular dimensions. A defining feature of zeolites is that their frameworks are made up of 4-coordinated atoms forming tetrahedra. These tetrahedra are linked together by their corners and make a rich variety of beautiful structures. The framework structure may contain linked cages, cavities or channels, which are big enough to allow small molecules to enter. The system of large voids explains the consistent low specific density of these compounds. The aluminosilicate framework is negatively charged and can attract positive cations that reside in the cages as a framework ion and can compensate for the negative charge of the framework.

Adsorption as used herein refers to molecules entering and adsorbing in the pore and not on the surface of the zeolite.

The zeolite disclosed here is an example of a synthetic zeolite with a CDO framework type. Molecular sieves are classified by the Structure Commission of the International Zeolite Association (IZA) according to the rules of the IUPAC Commission on Zeolite Nomenclature. According to this classification, framework type zeolites and other crystalline microporous molecular sieves, for which a structure has been established, are assigned a three letter code and are described in the "Atlas of Zeolite Framework Types," Sixth Revised Edition, Elsevier (2007).

CDO framework type molecular sieves, or zeolites, are characterized by two-dimensional 8-membered-ring pore/channel systems and a interconnecting cage. Zeolite CDO is a small pore zeolite containing channels less than 3.1 angstrom in diameter and cages less than 5.0 angstrom in length.

Thus, CDO has a small pore opening that can discriminate between small molecules but a larger cage that can give the zeolite high adsorption capacity.

In one embodiment, the zeolite CDO has a pure silica composition.

In one embodiment the zeolite CDO is formed into the adsorbent particles by pressing into pellets. In one embodiment, the adsorbent particles can be a component in a membrane that is used for removing the impurities from the feed gas stream that is ethylene-rich. Some examples of mixed-matrix membranes with dispersed adsorbent particles are described in U.S. Pat. No. 6,508,860.

In one embodiment, the zeolite CDO can be formulated into the adsorbent particles using a combination with other materials, such as binders and/or matrix materials, which provide additional hardness or adsorbent activity to the adsorbent particles. When used, the relative proportions of the zeolite CDO and other materials may vary widely with the zeolite or molecular sieve content ranging from 1 to 90 wt %, or from 2 to 80 wt % of the adsorbent particles.

In one embodiment, the adsorbent particles are made from a homogeneous mixture and are not coated particles or made from layers of different materials. An example of how these adsorbent particles can be made is when the adsorbent particles are pressed into pellets from a powder. In one embodiment, the zeolite is mixed with a catalyst support and the zeolite and the catalyst support are ground together into a powder that is a homogeneous mixture. In one embodiment the catalyst support is alumina, such as a pseudo-Boehmite alumina powder. The catalyst support can be inert or can participate in the adsorption performed by the adsorbent particles. Typical catalyst supports include various kinds of carbon, alumina, and silica. In one embodiment, the catalyst support comprises an amorphous silica aluminate. In one embodiment, the catalyst support comprises an amorphous silica aluminate and a second support material.

Examples of the catalyst support or the second support material (when used), can include kieselguhr, alumina, silica, and silica-alumina. Other examples include alumina-boria, silica-alumina-magnesia, silica-alumina-titania and materials obtained by adding other zeolites and other complex oxides thereto. In one embodiment, the catalyst support is porous, and comprises a natural clay or a synthetic oxide. The catalyst support can be selected to provide adequate mechanical strength and chemical stability at the contacting conditions under which the adsorbent particles are employed.

In one embodiment, the catalyst support or the second support material comprises a pseudo-boehmite alumina. Examples of pseudo-boehmite alumina are CATAPAL® high purity aluminas CATAPAL® is a registered trademark of Sasol Limited. The pressed pellets can be broken and sieved to obtain the desired mesh size. In one embodiment, the powder X-ray diffraction (XRD) pattern of the pressed pellets is the same as the original XRD pattern of the zeolite powder prior to it having been pressed into a pellet.

In one embodiment, the method comprises alternating an input of the feed gas stream between at least two beds of the one or more adsorbent particles. In one embodiment, the at least two beds of the one or more adsorbent particles are up to ten beds of the one or more adsorbent particles. The feed gas stream can contact one of the at least two beds at a given time by an adsorption step and a product gas stream can be simultaneously vented from another of the at least two beds by a desorption step to recover high purity ethylene.

In one embodiment, the desorbed high purity ethylene product stream is compressed to from about 500 to 700 psia and recycled to a polyethylene reactor.

Figure 16:
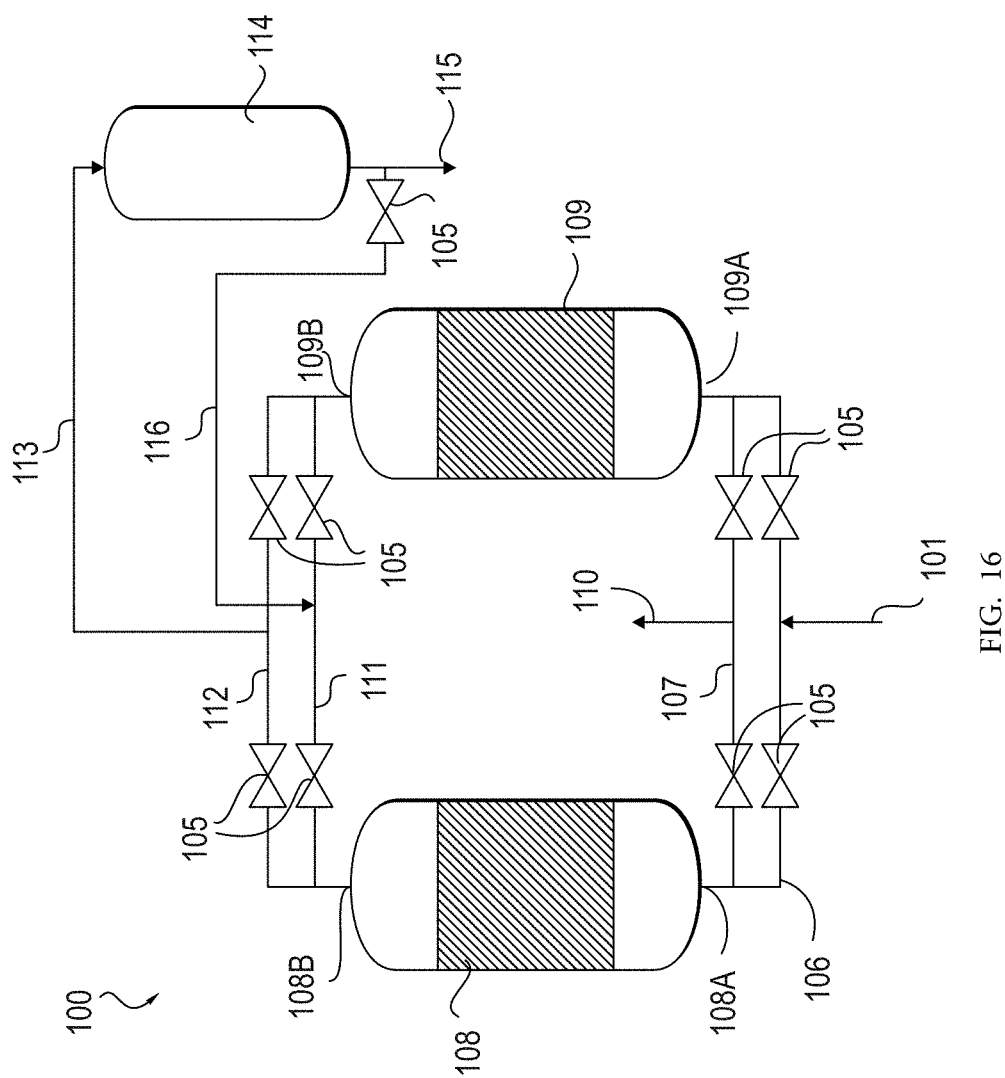
FIG. 16 is a diagram of an exemplary two bed PSA system.

Referring to FIG. 16, here is shown an exemplary two bed PSA system (100) with two beds. In this figure, a feed gas stream (101) is introduced into line (106) having block valves (105) therein. Line (106) connects the first inlet end (108A) to the first adsorption column (108), and also connects the second inlet end (109A) to the second adsorption column (109). A second line (107), is fluidly connected to line (106) and separately connects the first inlet end (108A) to the first adsorption column (108), and also connects the second inlet end (109A) to the second adsorption column (109). Second line (107) has an outlet for tail gas (110). The first adsorption column (108) contains the adsorbent particles described herein, and has a first product end (108B). The second adsorption column (109) also contains the adsorbent particles described herein, and has a second product end (109B). The first product end (108B) and the second product end (109B) are connected by a third line (111) and by a fourth line (112). The third line (111) and the fourth line (112) contain block valves (105). The fourth line (112) is connected with a fifth line (113), which delivers an intermediate product gas stream to a product gas buffer tank (114). The product gas buffer tank (114) allows for controlled purging and re-pressurization steps. The product gas stream (115) can be provided from the product gas buffer tank (114). The product gas buffer tank is controlled by one or more block valves (105) through a sixth line (116) that connects to the third line (111), as shown.

In one embodiment, wherein the method utilizes two beds of the one or more adsorbent particles, the method further comprises:

a. following the adsorption step in one of the two beds and a simultaneous desorption step in the other of the two beds, equalizing a pressure of the two beds through the product end of each of the two beds at the end of the adsorption and the simultaneous desorption step; and b. re-pressurizing the bed having just completed the simultaneous desorption step by sending a slipstream of the product gas stream through the product end of the bed having just completed the simultaneous desorption step.

EXAMPLES

Example 1: Unseeded Synthesis of RUB-36

Following reference 1, 3.0 grams of tetraethylorthosilicate (TEOS) was mixed with 9.73 g of methyltriethylammonium hydroxide (20 wt % in water) in a 23 mL Teflon reactor. The solution was stirred covered at room temperature overnight to allow for hydrolysis of the TEOS. Then, the solution was uncovered and ethanol and water were allowed to evaporate to a final mass of 4.807 g. 0.60 g of hydrofluoric acid (48%) was added to the solution with manual mixing (Caution: Use all appropriate safety precautions when working with HF). The final molar ratios were: $1SiO_2:1ROH:1HF:10H_2O$. The reactor was closed and placed in an oven tumbling at 43 rpm and 170° C. for 5 days. The product was recovered by filtration and washed extensively with water. The XRD pattern of the product is shown in FIG. 1.

Example 2: Seeded Synthesis of RUB-36

10.0 grams of tetraethylorthosilicate (TEOS) was mixed with 9.73 g of methyltriethylammonium hydroxide (20 wt % in water). The solution was stirred covered at room temperature overnight to allow for hydrolysis of the TEOS. Then, the solution was uncovered and ethanol and water were allowed to evaporate to a final mass of 16.02 g. The solution was divided into 2 23 mL Teflon reactors, and 1.0 g of hydrofluoric acid (48%) was added to each solution with manual mixing (Caution: Use all appropriate safety precautions when working with HF). 0.400 g of RUB-36 from example 1 were added to each reactor, and the reactor was closed and placed in an oven tumbling at 43 rpm and 170° C. for 5 days. The final molar ratios were: $1SiO_2:1ROH:1HF:10H_2O$. The product was recovered by filtration and washed extensively with water. The XRD pattern of the product is similar to that in FIG. 1.

Example 3: Calcination of RUB-36 to CDO

Figure 2:
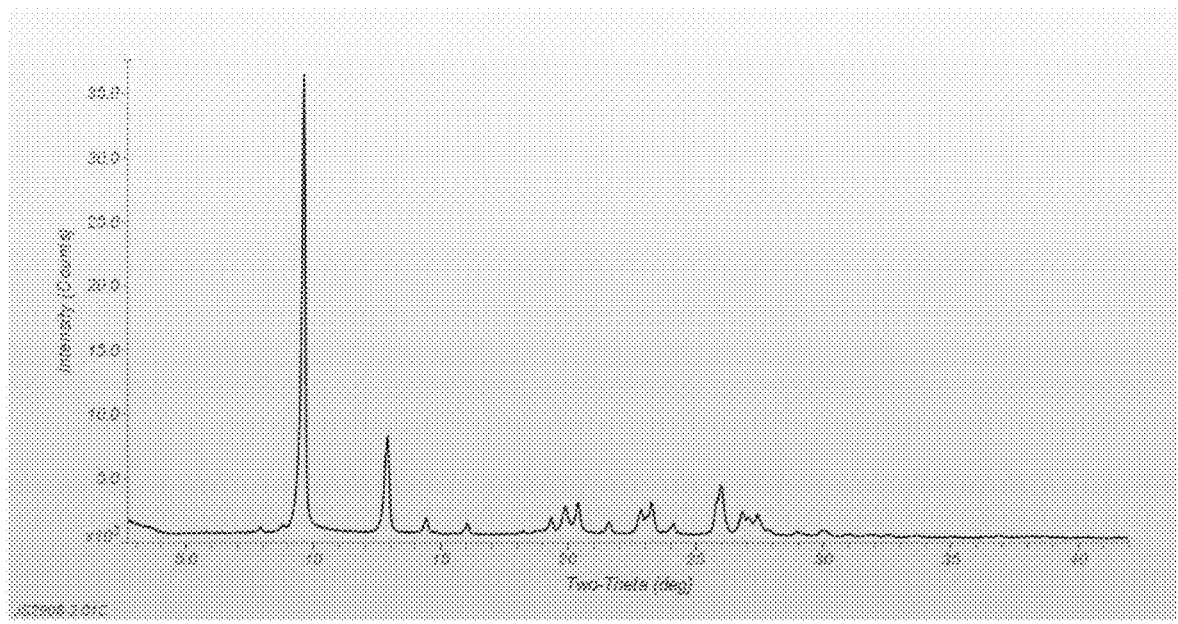
FIG. 2 is a XRD pattern of as made CDO.

The material from example 2 was calcined in air (250 sccm) at 595° C. by ramping to 120° C. (1° C./min) and holding for 2 hours, then ramping to 540° C. (1° C./min) and holding for 5 hours, then ramping to 595° C. (1° C./min) and holding for 5 hours and finally cooling to room temperature. After calcination the material had transformed into CDO by topotactic condensation. The XRD pattern is shown in FIG. 2, and the nitrogen micropore volume was measured to be 0.11 cc/g (t-plot method) with a BET surface area of 312.22 m2/g. This sample is referred to as CDO-1.

Example 4: Synthesis of CDS-1

Figure 3:
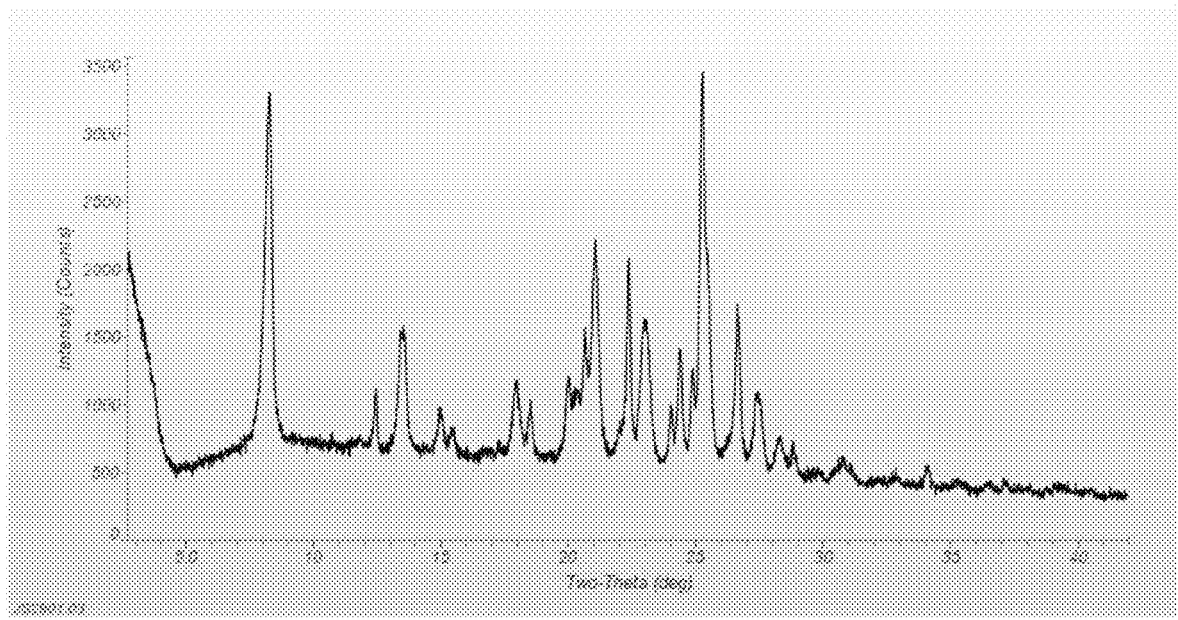
FIG. 3 is a XRD pattern of as-made CDS-1.

Following references 2 and 3, 33.7 g of water was mixed with 13.25 g of 25 wt % tetramethylammonium hydroxide and 0.25 g of 1 M KOH. Then 10.5 g of Cab-O-Sil M5 silica gel was added and mixed well. Finally 50 g of 1,4-dioxane was added and the mixture was charged in a 125 mL Teflon lined Parr reactor and heated statically at 150° C. for 23 days. The product was recovered by filtration and washed extensively with water. The XRD pattern of the product is shown in FIG. 3.

Example 5: Calcination of CDS-1

Figure 4:
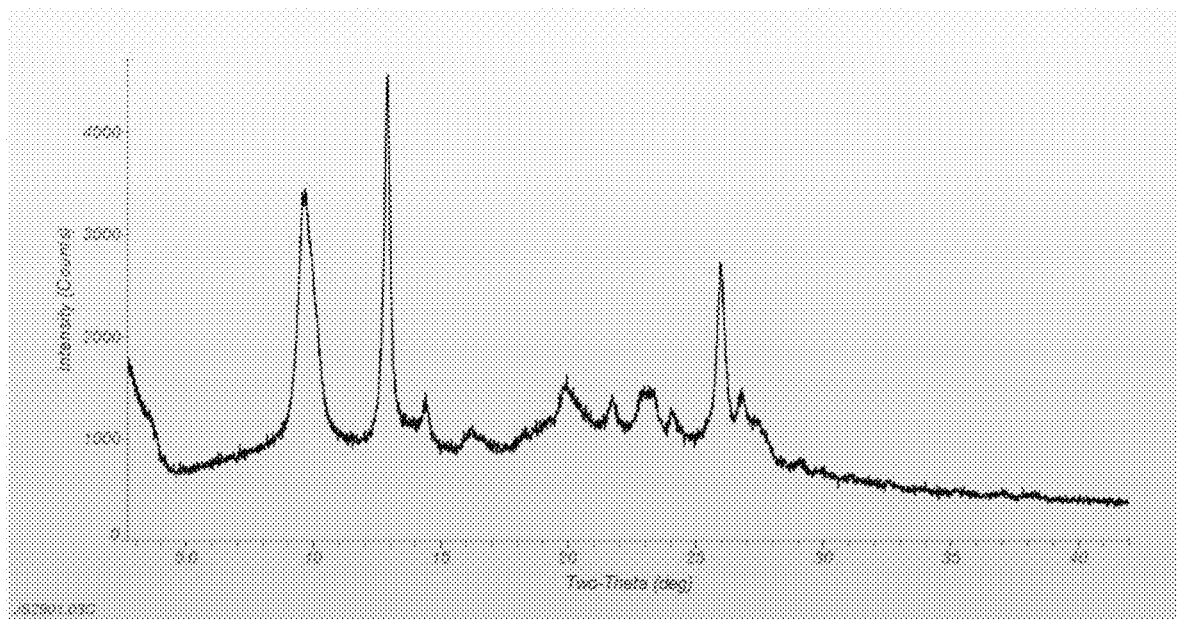
FIG. 4 is a XRD pattern of calcined CDS-1

The CDS-1 made in example 4 was calcined under the same conditions described in example 3. A XRD pattern of the product is shown FIG. 4. This sample is referred to as CDO-2. The measured nitrogen micropore volume from t-plot method is 0.096 cm3/g.

Comparative Example: Synthesis of RTH

Figure 5:
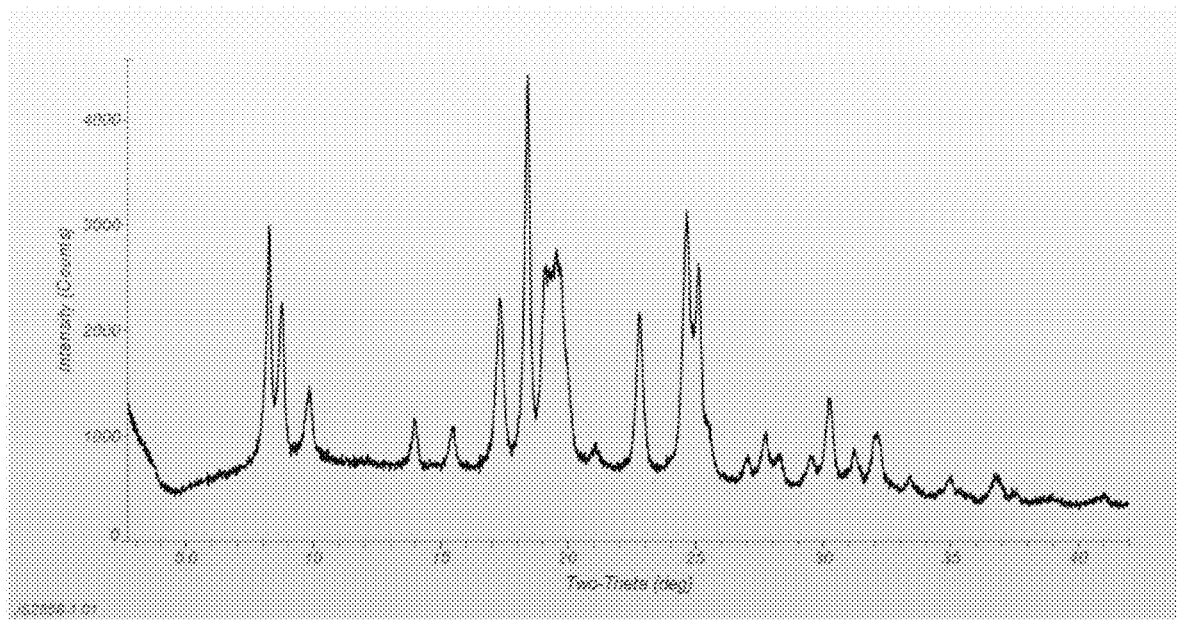
FIG. 5 is a XRD pattern of as-made RTH zeolite.
Figure 6:
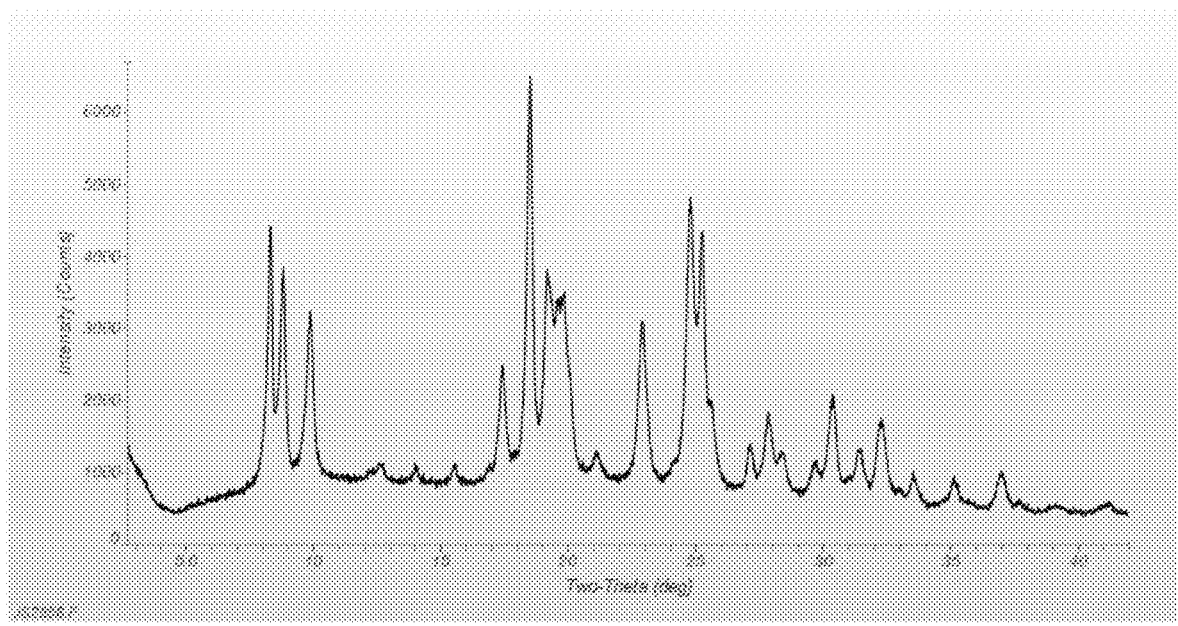
FIG. 6 is a XRD pattern of ammonium form RTH

Following reference 4, into a 23 mL Teflon the following were added: 2 g of 1 N NaOH, 10.9 g of a solution of pentamethylimidazolium hydroxide (0.55 mmol OH/g), 1.1 g of water and 2 g of CBV720 Y zeolite (Zeolyst). 60 mg of as-made RTH was added as seeds and the reactor contents were well stirred, charged in a Parr reactor and the reactor was closed and placed in an oven tumbling at 43 rpm and 160° C. for 14 days. The product was recovered by filtration and washed extensively with water. The XRD pattern of the product is shown in FIG. 5. This is a comparative 2-dimensional, 8-membered ring zeolite material, referred to as SSZ-36.

Example 7: Calcination and Ammonium Exchange of RTH Zeolite

The RTH made in example 6 was calcined under the same conditions described in example 3. The material was converted to ammonium form using a 10 wt % aqueous solution of ammonium nitrate with the same mass of ammonium nitrate used as zeolite, the solution was held at 85° C. for 3 hours and then filtered. This was repeated twice, for a total of 3 exchanges. After the final exchange the material was washed with water until the conductivity of the wash water was less than 50 μS/cm and the material was dried in air at 85° C. A XRD pattern of the product is shown FIG. 4. The final product was determined to have a Si/Al ratio of 13.3 and nitrogen micropore volume of 0.21 cc/g (t-plot method).

Example 8: Pure Component Equilibrium Adsorption on CDO Samples

Equilibrium gas adsorption experiments for $C_2H_4$ and $C_2H_6$ were performed on a HPVA 200-4 port volumetric system. Samples were first activated at 300° C. to obtain the dry weight and then reactivated in the gas adsorption system. Gases used were $C_2H_4$, $C_2H_6$, and He (all 99.999%). The zeolite was tested from 0-10 bar for both $C_2H_4$ and $C_2H_6$.

Figure 7:
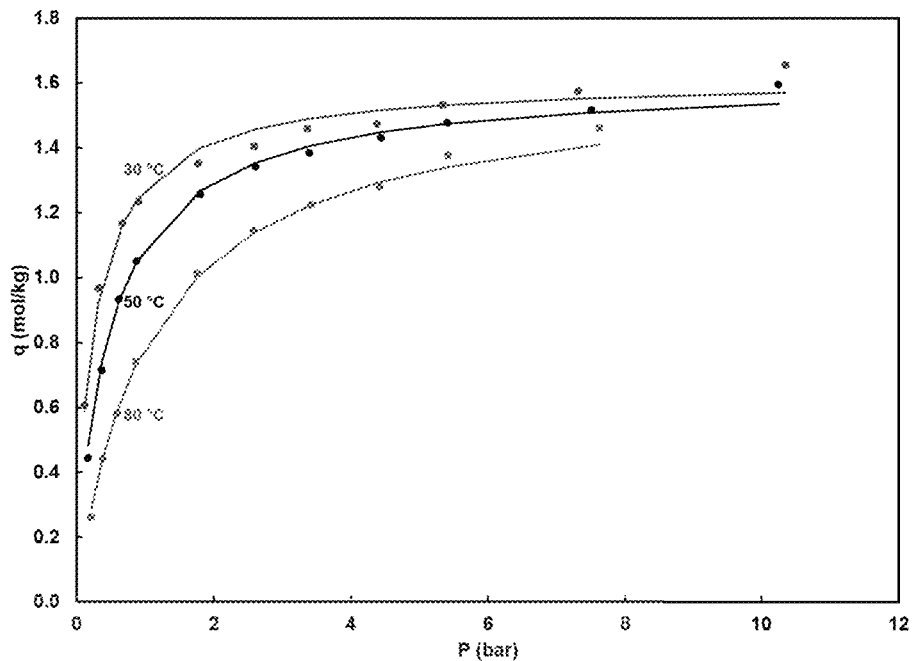
FIG. 7 is a plot of gas adsorption isotherms of C2H4 at 30, 50 and 80 degrees C. for CDO-1.
Figure 8:
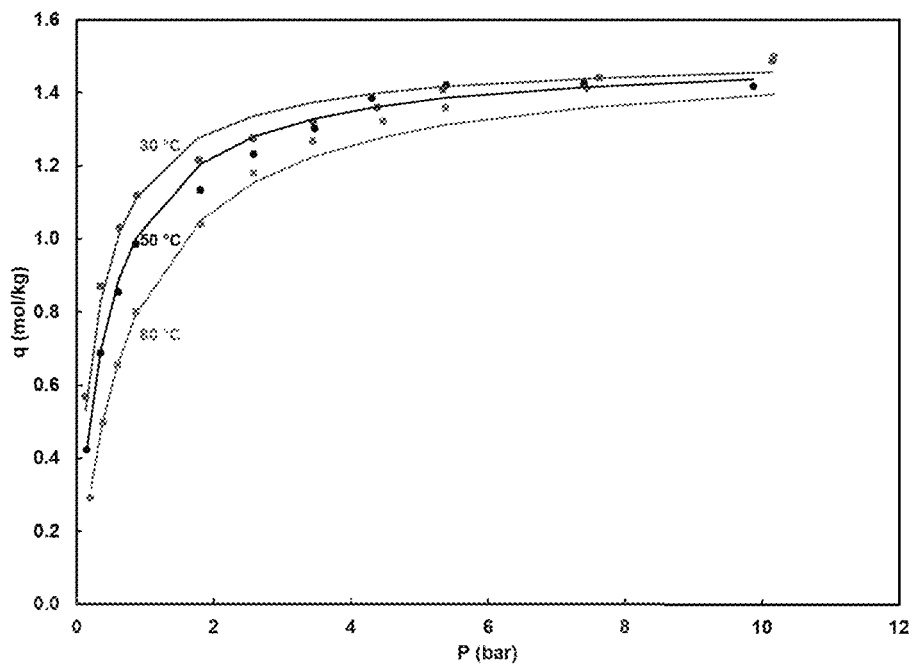
FIG. 8 is a plot of gas adsorption isotherms of C2H6 at 30, 50 and 80 degrees C. for CDO-1.

FIG. 7 shows the equilibrium adsorption results for gas adsorption tests of ethylene for CDO-1 sample synthesized with Example 3 with varying temperatures. FIG. 8 shows equilibrium adsorption results for gas adsorption tests of ethane for CDO-1 sample. As shown, there is a higher adsorption affinity for ethylene in CDO over ethane, despite being a pure silica zeolite framework material. Based on the calculated Henry's constants for ethylene and ethane, CDO-1 exhibits an ideal adsorption selectivity of 1.4, summarized in Table 1.

Figure 9:
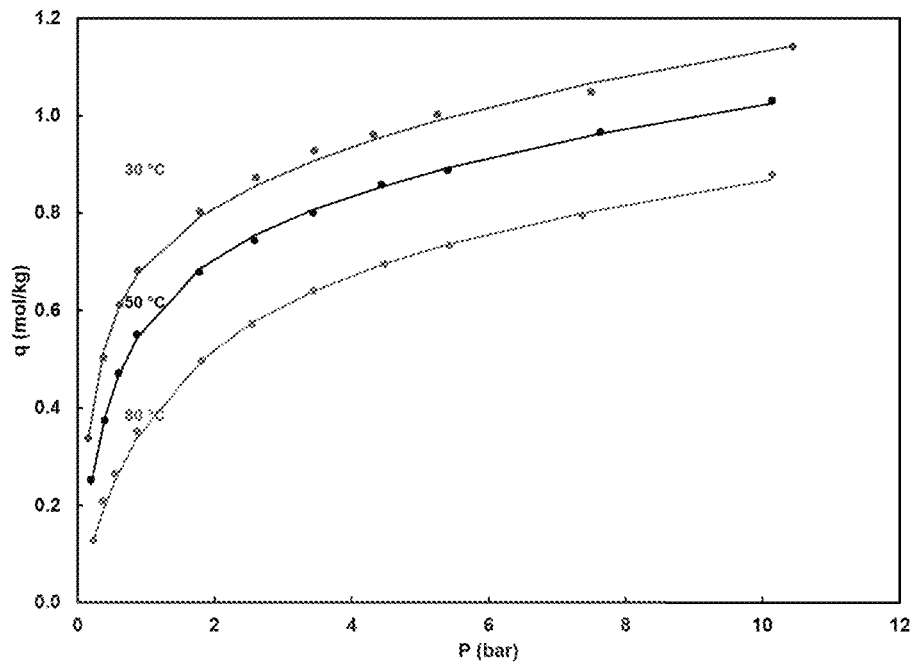
FIG. 9 is a plot of gas adsorption isotherms of C2H4 at 30, 50 and 80 degrees C. for CDO-2.
Figure 10:
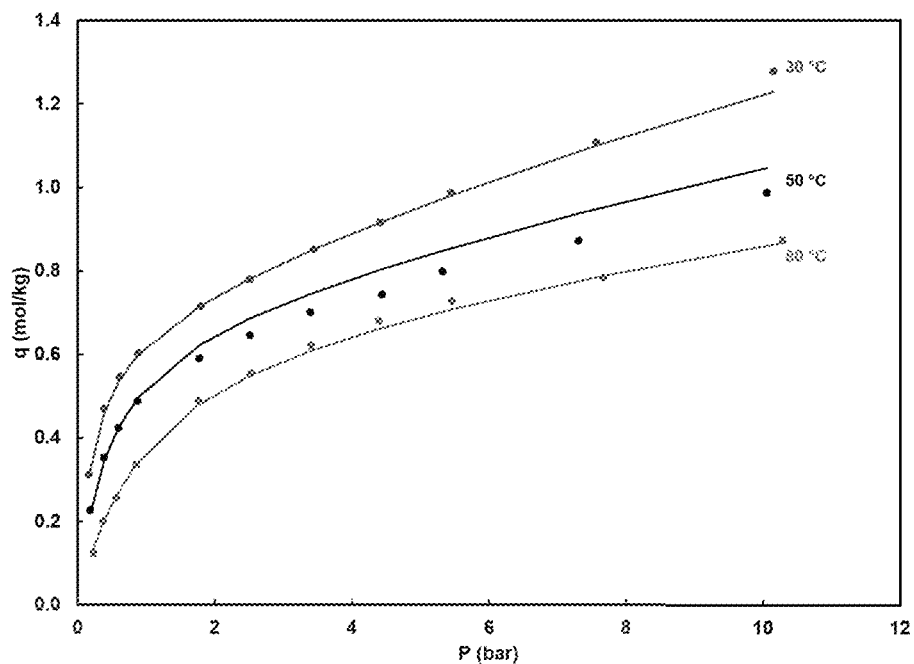
FIG. 10 is a plot of gas adsorption isotherms of C2H4 at 30, 50 and 80 degrees C. for CDO-2.

FIG. 9 shows the equilibrium adsorption results for gas adsorption tests of ethylene for CDO-2 sample synthesized with Example 5 with varying temperatures. FIG. 10 shows equilibrium adsorption results for gas adsorption tests of ethane for CDO-2 sample. There is less total adsorption capacity for both ethylene and ethane in CDO-2 samples compared to CDO-1. This can be attributed to the lower measured micropore volume for CDO-2. In general, the reduction in gas uptake is proportional to the micropore volume differences. However, the difference in synthesis does not affect the overall ideal adsorption selectivity negatively. For the CDO-2 sample, the Henry's constants show a ratio of 1.1.

Example 9: Kinetic Uptake of CDO and RTH Adsorbents

Figure 11:
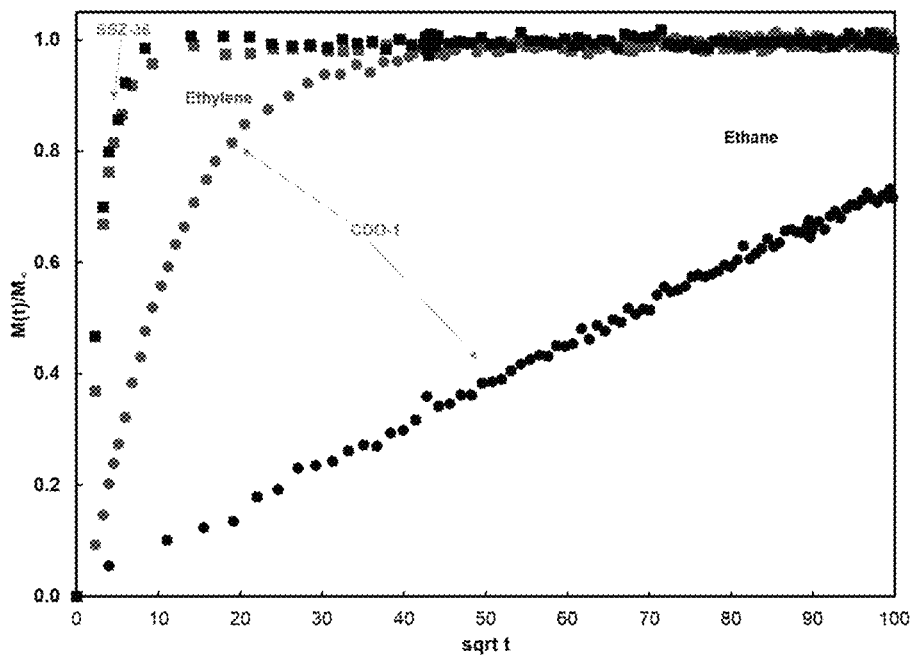
FIG. 11 is a plot of kinetic uptake of C2H4 and C2H6 on CDO-1 sample and a comparative zeolite sample, SSZ-36, at 30 degrees C.
Figure 12:
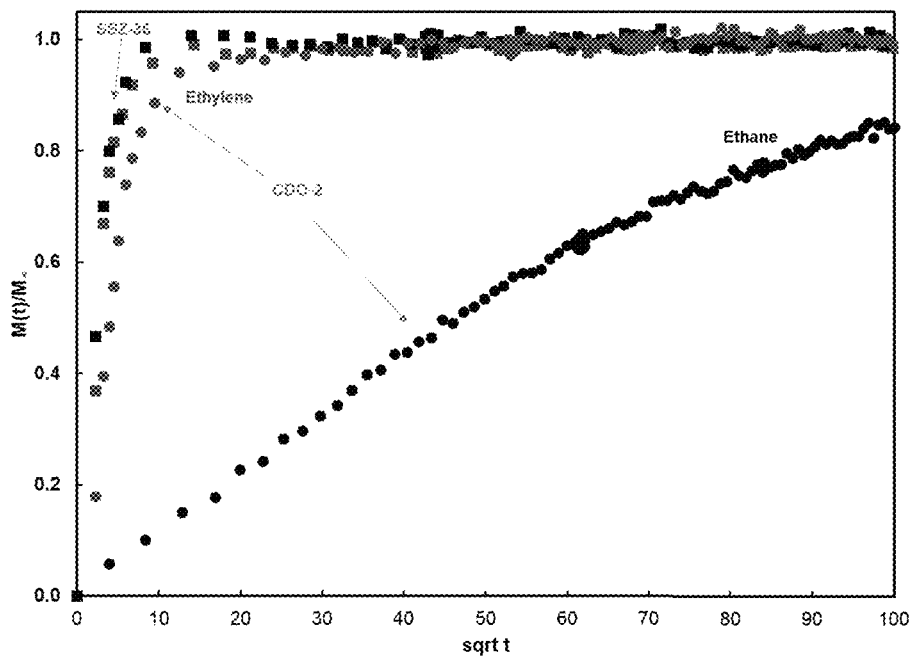
FIG. 12 is a plot of the kinetic uptake of C2H4 and C2H6 on CDO-2 sample and a comparative zeolite sample, SSZ-36, at 30 degrees C.

Molecular sieving effects in the adsorption uptake of larger molecules found as impurities in ethylene streams such as ethane, propane and isobutane, relative to uptake of ethylene, plays an important role in recovery of ethylene from ethylene-stranded gases. CDO-1 demonstrates the ability to selectivity adsorb ethylene faster than ethane without any material or synthesis modification, likely due to the unique zeolite pore window and cage structures. This gas pair is important in recovery of ethylene from stranded ethylene-containing gases as molecules with two or more carbons can be difficult to remove if adsorbed onto the adsorbent material. Slow uptake allows the cycling of adsorbent to prevent complete uptake and maintain separation of the slower-adsorbing compounds during adsorption. FIG. 11 shows kinetic uptake of C2H4 and C2H6 of CDO-1 and a comparative zeolite, SSZ-36. As shown in FIG. 11, uptake of C2H4 is relatively fast for both zeolite materials; however, ethane kinetic uptake in CDO-1 is comparatively slow compared to SSZ-36.

Kinetic uptake and kinetic selectivity for ethylene over ethane is also observed in CDO-2 sample. In this case, the kinetic uptake is faster compared to CDO-1, but still exhibits diffusion selectivity for ethylene over ethane in the CDO-2 sample. In addition, the uptake of ethylene is as fast as SSZ-36.

Combination of both the equilibrium and the kinetic selectivity can yield the overall cyclic kinetic adsorption performance of a material. Table 1 shows the Henry's adsorption constants and diffusion constants calculated from the adsorption equilibrium and kinetics data for CDO-1 and CDO-2. The PSA selectivity in Table 1 is described in D. M. Ruthven and S. C. Reyes, "Adsorptive Separation of Light Olefins from Paraffins", Microporous and Mesoporous Materials, 2007, 104, 59-66. Both CDO-1 and CDO-2 demonstrate that the PSA selectivity exceeds 10, based on the calculated diffusion and adsorption constants. This suggests that the CDO structure provides high PSA selectivity toward ethylene over ethane, despite differences in equilibrium adsorption properties due to the PSA selectivity dependence on the ratio of the diffusion coefficients for the gas pair of interest.

TABLE 1

Summary of adsorption performance properties for C2H4 and C2H6 for CDO-1. D/r2 is the diffusion constant, K is the Henry's adsorption constant and α is the PSA selectivity.

| Sample | Gas | D/r2 (1/sec) | K (mol/kg/bar) | α (C2H4/C2H6) |
|---|---|---|---|---|
| CDO-1 | C2H4 | 4.57e−03 | 18.4 | 18 |
|  | C2H6 | 2.13e−05 | 13.4 |  |
| CDO-2 | C2H4 | 1.62e−02 | 3.84 | 15 |
|  | C2H6 | 9.04e−5 | 3.46 |  |

Example 10: Dynamic Column Breakthrough (DCB) Adsorption Performance

Figure 13:
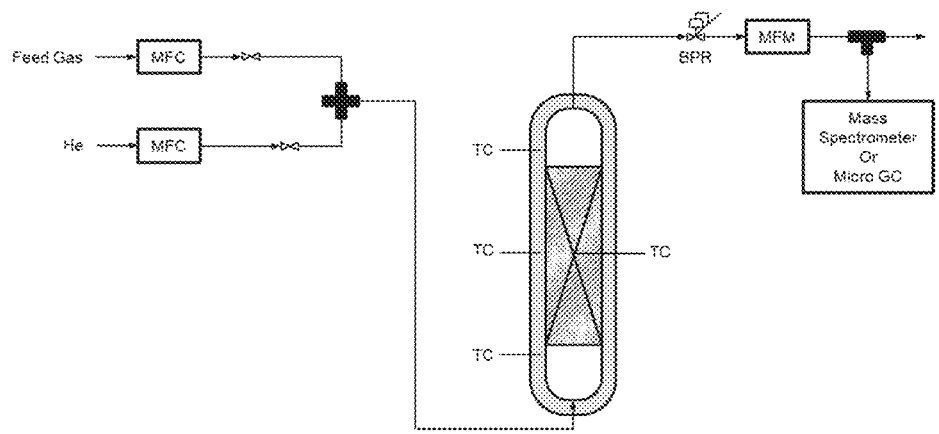
FIG. 13 is a diagram of the dynamic breakthrough column apparatus.

Dynamic adsorption experiments were carried out on a custom-built dynamic column breakthrough (DCB) apparatus, as shown in FIG. 13. Two lines 1 and 2 were provided for test gases to be fed to the apparatus and metered using mass flow controllers 3. Block valves 4 were provided for controlling flow in each line. A line 5 having heat tracing for controlling the temperature within the line delivered the test gases to an adsorption column 6 containing the adsorbent pellets therein. The adsorption column 6 was outfitted with a heater 9, specifically an electrically heated tape wrapped around the adsorption column, and a thermocouple 10. Line 11 removed treated gas from the column 6 Line 12 sent the treated gas to a back-pressure regulator 13. Pressure transducer 14 monitored the pressure in line 12. Mass flow meter 15 monitored the mass flow in line 12. The micro-gas chromatograph 16 monitored the peak areas of gases: helium, ethylene and ethane. The bulk bed temperature was monitored using one thermocouple 17 at approximately ½th the length of the bed during experiments, and the bed temperature was controlled by an external heating tape 9.

The adsorption capacity was determined by calculating the breakthrough time for ethylene by equation (1):

$$\tau_b = \int_0^\infty \left(1 - \frac{F_{i,o}}{F_{i,f}}\right) dt \quad (1)$$

where Fi is the molar flow rate of the gas component being considered at the outlet, o, and feed, f. To determine the breakthrough capacity, the methodology developed by Malek and Farooq in A. Malek, S. Farooq, "Determination of Equilibrium Isotherms Using Dynamic Column Breakthrough and Constant Flow Equilibrium Desorption", J. Chem. Eng. Data, 1996, 41, 25-32 was used. Using the methodology, the capacity is calculated by equation (2):

$$q_b = \frac{C_i}{\rho_p} \frac{\varepsilon_p}{1-\varepsilon_p} \left(\frac{v_i \tau_b}{l} - 1\right) \quad (2)$$

where qb is the breakthrough capacity, Ci is the gas step concentration of component i, $\rho_p$ is the particle density, $\varepsilon_p$ is the bed void fraction, vi is the interstitial velocity, l is the length of the packed bed and τp is the effective breakthrough time.

Figure 14:
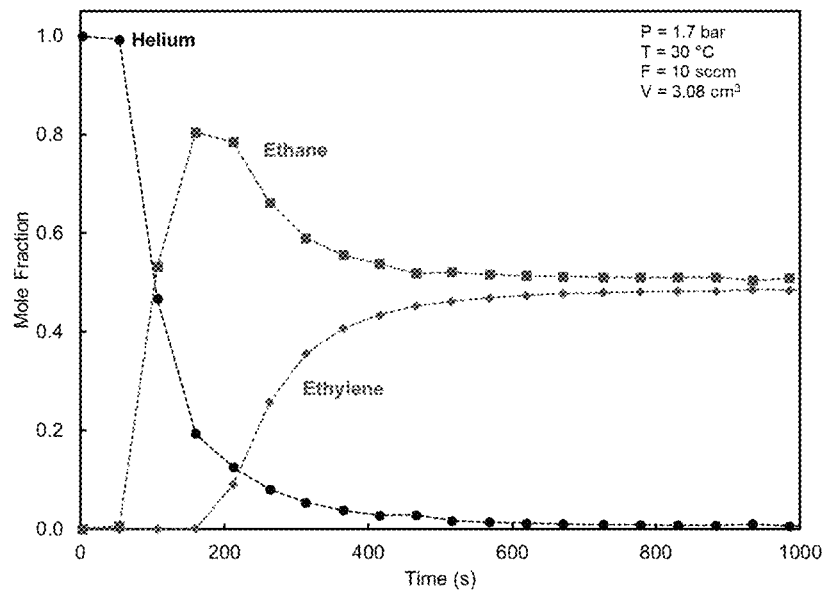
FIG. 14 is a plot of a multicomponent dynamic breakthrough experiment with 50:50 ethylene:ethane at 1.7 bar and 30° C.
Figure 15:
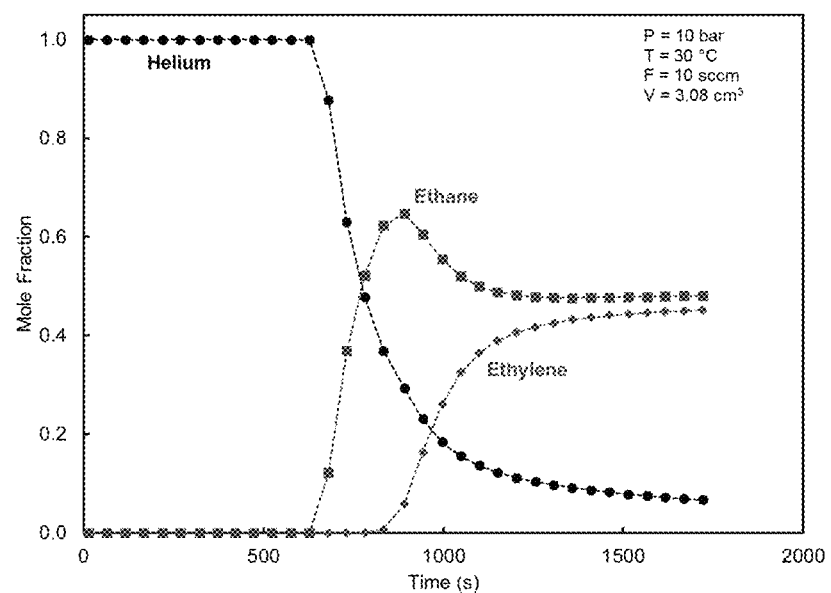
FIG. 15 is a plot of a multicomponent dynamic breakthrough experiment with 50:50 ethylene:ethane at 1.7 bar and 30° C.

A series of DCB experiments show the capability of CDO zeolites for separating ethylene and ethane gas mixtures. The sample used in these experiments is CDO-2, but as shown in other examples, it is expected to achieve similar or better separation performance for other methods of making the zeolite due to the inherent diffusion selectivity the zeolite structure has. FIGS. 14 and 15 show results of two DCB experiments. At a pressure of 1.7 bar, as shown in FIG. 14, there is clear separation between ethylene and ethane, and as the pressure is increased, the breakthrough curves show similar separation performance in FIG. 15. However, the maximum mole fraction for ethane decreased with the increase in feed pressure, reducing from 0.8 to 0.6. At elevated pressures, there may be increased dispersion of gas mixtures, resulting in spreading of the breakthrough curves for ethane and ethylene as well as the desorption curve for helium. The breakthrough curves in FIG. 15 suggests that dispersion may be playing a role in the observed mole fraction for these gas pairs.

The calculated breakthrough capacity for ethylene is very near to the pure component ethylene adsorption measured previously. At 1.7 bar, the multicomponent breakthrough capacity is calculated to be 0.604 mol/kg for ethylene while the pure component breakthrough capacity is 0.641 mol/kg. At 10 bar, the multicomponent breakthrough capacity is calculated to be 0.918 mol/kg while the pure component breakthrough capacity is 0.984 mol/kg. These results suggests that very little ethane is capable of adsorbing under these dynamic adsorption conditions.

The invention claimed is:

1. A method for removing impurities from a feed gas stream of ethylene-containing stranded gas including impurities and ethylene, comprising:

alternating an input of the feed gas stream between at least two beds of one or more adsorbent particles made from a homogeneous mixture, wherein the one or more adsorbent particles comprise a zeolite with CDO framework;

wherein the feed gas stream contacts one of the at least two beds at a given time by an adsorption step and a product gas stream is simultaneously vented from another of the at least two beds by a desorption step;

wherein the contacting of the one of the at least two beds by the feed gas stream occurs at a feed pressure of from about 345 kPa to about 3450 kPa for a sufficient time to preferentially adsorb the ethylene from the feed gas stream and thereby produces the product gas stream during the desorption step containing no greater than about 2 mol % impurities and at least about 98 mol % of the ethylene recovered from the feed gas stream; and wherein the feed gas stream is input at a feed end of each of the at least two beds, and an impurity-enriched gas stream is produced after adsorption of the ethylene and removed at the feed end, and wherein the product gas stream is removed at a product end of each of the at least two beds.

2. The method of claim 1, wherein the impurities are selected from the group consisting of nitrogen, hydrogen, propane, isobutane and ethane.

3. The method of claim 2, wherein the zeolite has a composition of pure silica in the framework.

4. The method of claim 1, wherein the method utilizes two beds of the one or more adsorbent particles, and further comprising:
 a. following the adsorption step in one of the two beds and a simultaneous desorption step in the other of the two beds, equalizing a pressure of the one of the two beds and the other of the two beds through the product end of each of the one of the two beds and the other of the two beds at an end of the adsorption step and the simultaneous desorption step; and
 b. re-pressurizing the other of the two beds having just completed the simultaneous desorption step by sending a slipstream of the product gas stream through the product end of the other of the two beds having just completed the simultaneous desorption step.

* * * * *